US012779114B2

(12) United States Patent
Desai et al.

(10) Patent No.: US 12,779,114 B2
(45) Date of Patent: Nov. 3, 2026

(54) LEVERED IV FLOW REGULATION CLAMP ASSEMBLY

(71) Applicant: CareFusion 303, Inc., San Diego, CA (US)

(72) Inventors: Aman Desai, Bengaluru (IN); Apurva Vikram Agarwal, Lucknow (IN); Amarsinh Deeliprao Jadhav, Bangalore (IN)

(73) Assignee: CAREFUSION 303, INC., San Diego, CA (US)

( * ) Notice: Subject to any disclaimer, the term of this patent is extended or adjusted under 35 U.S.C. 154(b) by 908 days.

(21) Appl. No.: 17/833,313

(22) Filed: Jun. 6, 2022

(65) Prior Publication Data

US 2023/0020041 A1 Jan. 19, 2023

Related U.S. Application Data

(60) Provisional application No. 63/223,436, filed on Jul. 19, 2021.

(51) Int. Cl.
*A61M 5/168* (2006.01)
*A61M 39/28* (2006.01)

(52) U.S. Cl.
CPC .... *A61M 5/16881* (2013.01); *A61M 5/16813* (2013.01); *A61M 39/284* (2013.01); *A61M 39/285* (2013.01)

(58) Field of Classification Search
CPC .. A61M 39/28; A61M 39/284; A61M 39/287; A61M 39/285; A61M 5/16813; A61M 5/16881; F16K 7/063; F16K 7/065; F16K 7/066; F16K 7/00
See application file for complete search history.

(56) References Cited

U.S. PATENT DOCUMENTS 3,034,504 A * 5/1962 Winsor ............. A61M 5/16886 604/254
4,285,492 A 8/1981 Bujan
4,676,476 A 6/1987 Herrli
5,402,823 A * 4/1995 Cole ....................... F16K 7/063 251/9
6,341,757 B1 * 1/2002 Starchevich ...... A61M 5/16881 251/6
8,308,128 B2 * 11/2012 Mackal ............... A61M 39/284 251/9

(Continued)

FOREIGN PATENT DOCUMENTS

JP S5988563 U 6/1984

OTHER PUBLICATIONS

International Search Report and Written Opinion for Application No. PCT/US2022/036125, dated Oct. 6, 2022, 17 pages.

(Continued)

*Primary Examiner* — Nilay J Shah
(74) *Attorney, Agent, or Firm* — MASCHOFF BRENNAN

(57) ABSTRACT

A levered flow regulation clamp assembly for adjusting the fluid flow rate in a connector tube of an infusion set is provided. The levered flow regulation clamp assembly includes a housing to receive the connector tube and a slider rotatably engaged within the housing and configured to compress the connector tube to provide a fluid flow adjustment. Infusion sets and methods of adjusting fluid flow rates are also provided.

19 Claims, 10 Drawing Sheets

(56) References Cited

U.S. PATENT DOCUMENTS

| | | | | |
|---|---|---|---|---|
| 8,313,081 | B2 | 11/2012 | Adelberg | |
| 8,544,815 | B2 | 10/2013 | Avery et al. | |
| 9,839,748 | B2 | 12/2017 | Ng et al. | |
| 2006/0129110 | A1* | 6/2006 | Smith ................ | A61M 39/287 604/250 |
| 2006/0169934 | A1 | 8/2006 | Werth | |
| 2008/0029721 | A1* | 2/2008 | Miyahara ............ | A61M 39/287 251/6 |
| 2008/0290303 | A1 | 11/2008 | Mackal | |
| 2009/0143723 | A1 | 6/2009 | Szpara et al. | |
| 2016/0114148 | A1 | 4/2016 | Holm et al. | |
| 2017/0120040 | A1* | 5/2017 | Burkholz ............ | A61M 39/288 |
| 2020/0324103 | A1 | 10/2020 | Pak et al. | |

OTHER PUBLICATIONS

Brazilian Office Action for Application No. BR112023027518-0, dated Mar. 24, 2026, 5 pages including translation.
Japanese Office Action for Application No. 2024-500273, dated May 7, 2026, 7 pages including translation.
India Office Action for Application No. 202317089925, dated Jul. 13, 2026, 7 pages.

* cited by examiner

LEVERED IV FLOW REGULATION CLAMP ASSEMBLY

CROSS-REFERENCES TO RELATED APPLICATIONS

This Application claims the benefit of U.S. Provisional Patent Application No. 63/223,436 entitled "LEVERED IV FLOW REGULATION CLAMP ASSEMBLY," filed on Jul. 19, 2021, the disclosure of which is hereby incorporated by reference in its entirety for all purposes.

TECHNICAL FIELD

The present disclosure generally relates to a gravity intravenous (IV) set or infusion pump flow control device, and in particular a lever operated IV flow regulation clamp assembly.

BACKGROUND

Flow controllers in the form of roller clamps are used in the medical field for IV applications. Roller clamps are found on standard administration sets and are attached during the manufacturing process. Typical roller clamps control a flow rate through an IV tube by clamping an IV tube in between a roller wheel and a housing, allowing the tube to be incrementally occluded by pinching the tubing as the roller clamp is tightened. Most roller clamps are easily regulated with one hand, where the preferred process is to completely close the roller clamp and regulate the rate by rolling the clamp upward to open it. The wheel of the roller clamp is maintained at its place because of transient fit with the roller body, engagement of tubing with the wheel and friction of wheel with the roller body. However, over a period at high flow rate the wheel tends to drift away from its set position and cause an inaccurate rate of fluid delivery.

Thus, it is desirable to provide a levered flow regulation clamp assembly that provides structural stability with the ability to control the flow consistently without variation in the adjusted flow rate.

SUMMARY

One or more embodiments provide a levered flow regulation clamp assembly. The flow regulation clamp assembly includes a housing having an open-ended structure and having two opposing side walls, each side wall comprising a rectangular bottom portion and a curvilinear top portion and a bottom wall connecting the side walls, the side walls and the bottom wall defining a housing channel, and a bottom portion of the housing channel defining a tube channel configured to receive an intravenous tube. The flow regulation clamp assembly also includes a slider coupled to the housing, the slider including a body, a cam disposed at a first end of the body, a gripping portion disposed at a second end of the body and two opposing axles rotatably disposed within associated axle openings in the opposing side walls of the housing, wherein the body of the slider is configured to rotate about the opposing axles in the housing channel between an open position and a closed position.

One or more embodiments provide a gravity infusion set including a drip chamber, a connector tube and a levered flow regulation clamp assembly. The levered flow regulation clamp assembly includes a housing having an open-ended structure and having two opposing side walls, each side wall comprising a rectangular bottom portion and a curvilinear top portion and a bottom wall connecting the side walls, the side walls and the bottom wall defining a housing channel, and a bottom portion of the housing channel defining a tube channel configured to receive an intravenous tube. The levered flow regulation clamp assembly also includes a slider coupled to the housing, the slider including a body, a cam disposed at a first end of the body, a gripping portion disposed at a second end of the body and two opposing axles rotatably disposed within associated axle openings in the opposing side walls of the housing, wherein the body of the slider is configured to rotate about the opposing axles in the housing channel between an open position and a closed position.

One or more embodiments provide a method of operating a levered flow regulation clamp assembly, the method including disposing an intravenous tube within the levered flow regulation clamp assembly by extending the intravenous tube through a length of a bottom portion of a housing channel defining a tube channel; engaging a gripping portion of a slider coupled to the housing, the slider being in an open flow position in which the slider is one of not contacting the intravenous tube and contacting but not impinging the intravenous tube to provide full fluid flow through the intravenous tube; rotating the slider in a first rotational direction along a top curvilinear portion of the housing channel to a desired flow position, thus rotating a cam disposed on an end of the slider downward into the tube channel a defined distance of travel associated with a degree of rotation of the slider; pushing a contact surface of the cam into the intravenous tube the defined distance of travel, thus occluding the intravenous tube a defined amount associated with a defined reduced fluid flow rate through the intravenous tube; and leaving the slider in the desired flow position, wherein the slider is self-locking based on a frictional force from a friction pad disposed on at least one of the slider and the top curvilinear portion of the housing channel, the frictional force being greater than a rotational tendency of the cam from fluid forces pushing the intravenous tube against the cam.

The foregoing and other features, aspects and advantages of the disclosed embodiments will become more apparent from the following detailed description and accompanying drawings.

BRIEF DESCRIPTION OF THE DRAWINGS

The accompanying drawings, which are included to provide further understanding of the disclosure and are incorporated in and constitute a part of this specification, illustrate embodiments of the disclosure and together with the description serve to explain the principles of the disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Roller clamps are typically found on all standard administration sets and are attached during the manufacturing process. The roller clamp allows the tube to be incrementally occluded by pinching the tubing as the roller clamp is tightened. Most roller clamps are easily regulated with one hand. The preferred process is to completely close the roller clamp and regulate the rate as the clamp roller is rolled upward to open it. The clamp is designed to hold its place on the tubing, keeping the infusion rate constant between adjustments.

The wheel of the roller clamp is maintained at its place because of transient fit with the roller body, engagement of tubing with the wheel and friction of wheel with the roller body. Over a period at high flow rate the wheel drifts away from its set position and cause an inaccurate rate of fluid delivery to the patient.

Figure 1:
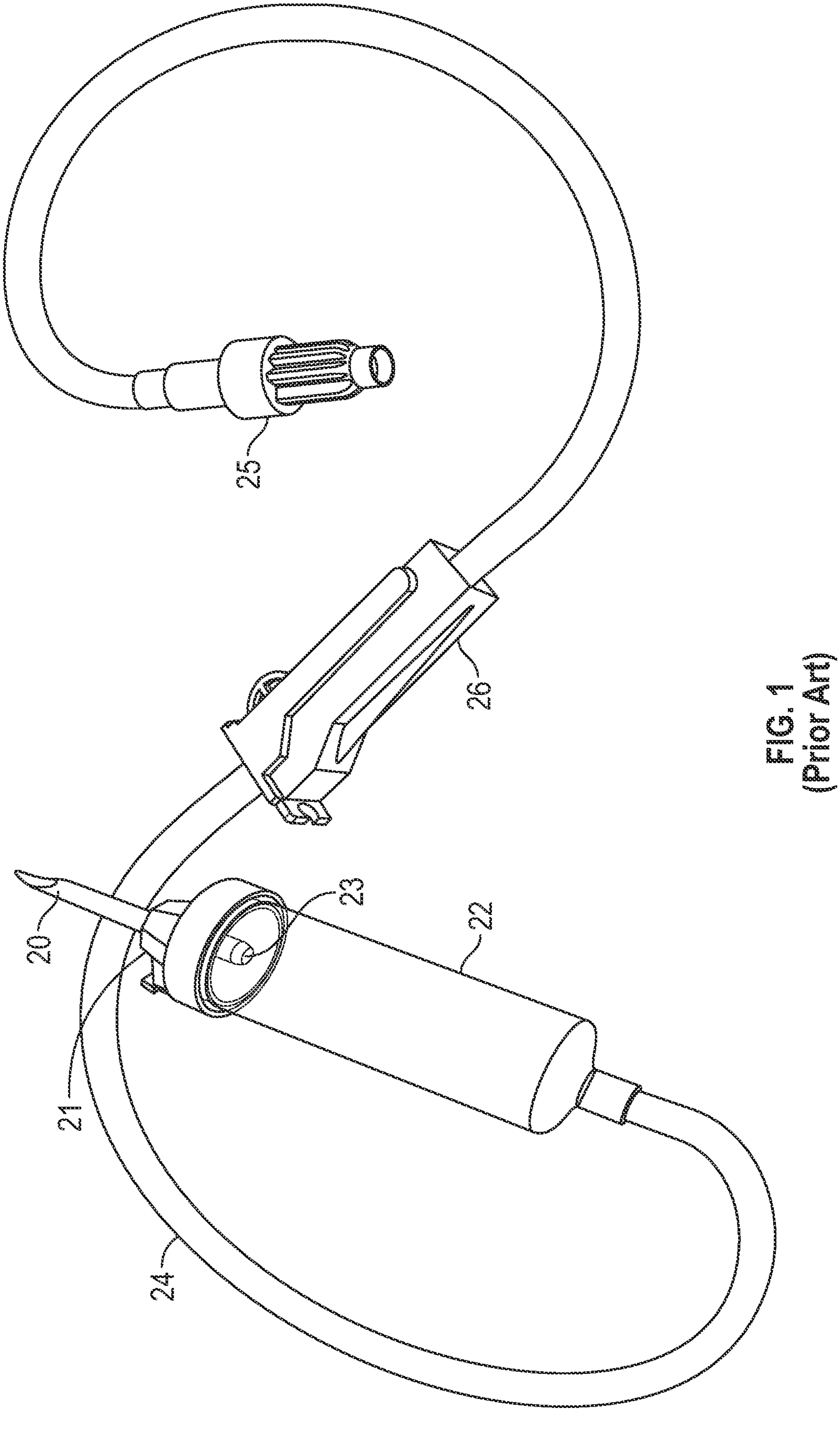
FIG. 1 (Prior Art)
FIG. 1 depicts a perspective view of an example infusion set having a typical roller clamp.

The present disclosure relates to a flow regulator and in particular to a levered IV flow regulation clamp assembly for use in IV sets. The flow regulation clamp regulates the flow rate of a medical fluid (for example a solution of a drug to be administered to a patient, or blood) flowing through a tube. Typically, a standard infusion set is used to infuse the fluid. An example of a standard infusion set is shown in FIG. 1.

The infusion set includes a piercing spike 20 which may either be a sharp spike for piercing rubber stoppers or rounded and blunt for insertion into a bag. The spike contains one channel for fluid and optionally a second channel for venting. A vent 21 is usually present in the vicinity of the piercing spike to allow air to flow into the drip chamber 22. The vent 21 may be provided with a bacterial filter to prevent bacteria from entering the equipment.

The drip chamber 22 has a drop generator 23 at the top of the drip chamber 22 that produces drops of a certain size. Drops from the drop generator 23 fall into the drip chamber 22 such that the drip chamber 22 is partially filled with liquid. This prevents air bubbles from entering the connector tube 24, which would be harmful to a patient. A particle filter may be provided at the lower aperture of the drip chamber 22.

The connector tube 24 connects the drip chamber 22 with a recipient of the liquid (e.g., a container or a patient). The connector tube 24 is usually around 150 cm long and can be manufactured from PVC. The tube 24 is shown shortened in FIG. 1 for clarity. The connector tube 24 typically has a continuous diameter throughout the length of the tube.

At the end of the connector tube 24 is a Luer fitting 25 which is standardized for connection to all other pieces of apparatus having a standard Luer cone. The person skilled in the art will appreciate that the Luer fitting 25 can be fitted to a hypodermic needle (not shown) for infusing the medical fluid into a container or into the circulatory system of a patient (e.g., into a vein).

Between the drip chamber 22 and the Luer fitting 25 and engaging with the connector tube 24, is a roller clamp 26. The present disclosure is concerned with an improved roller clamp assembly, but a typical roller clamp 26 as known in the art will now be described for background information.

Figure 2:
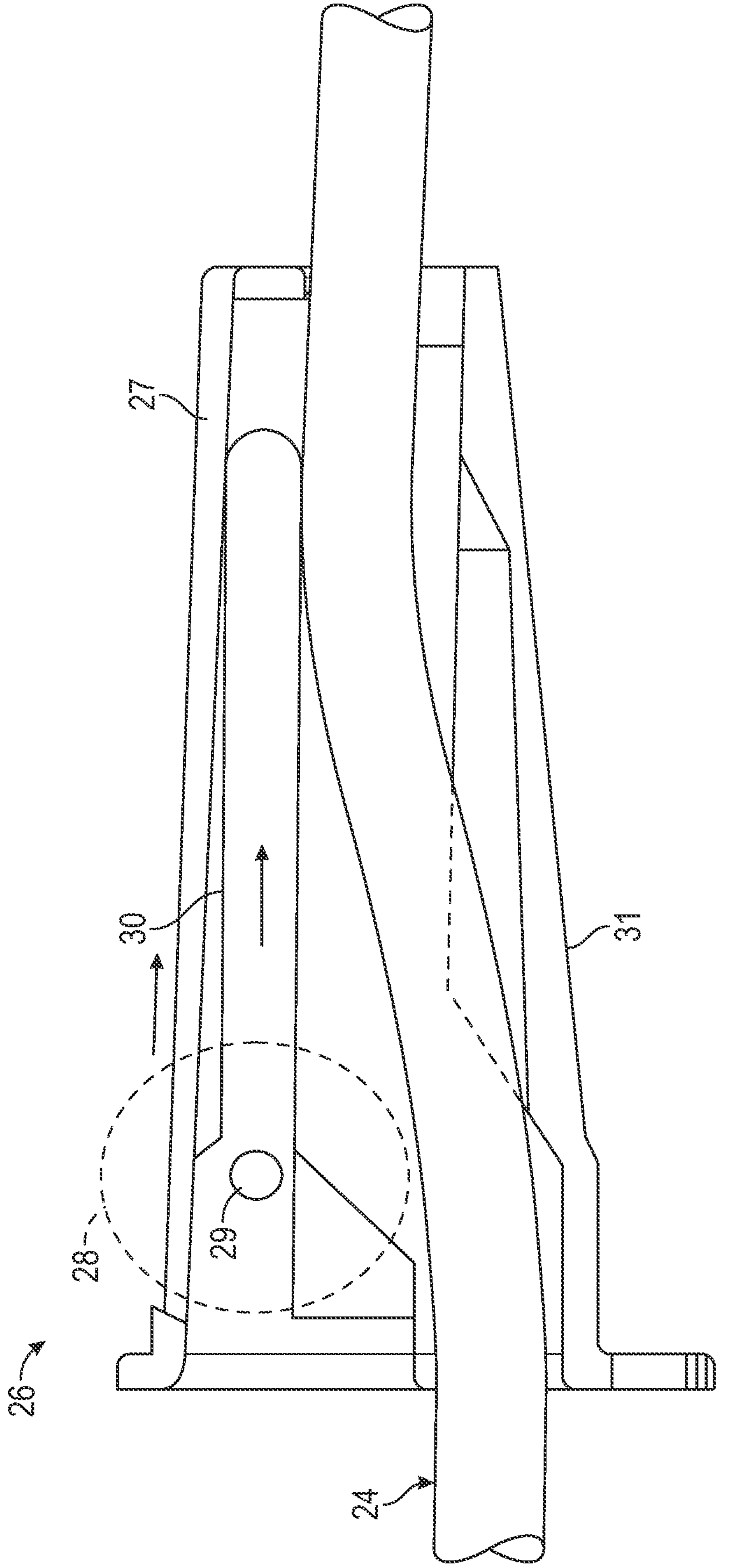
FIG. 2 (Prior Art)
FIG. 2 depicts a cross-section side view of the roller clamp of FIG. 1.
Figure 3:
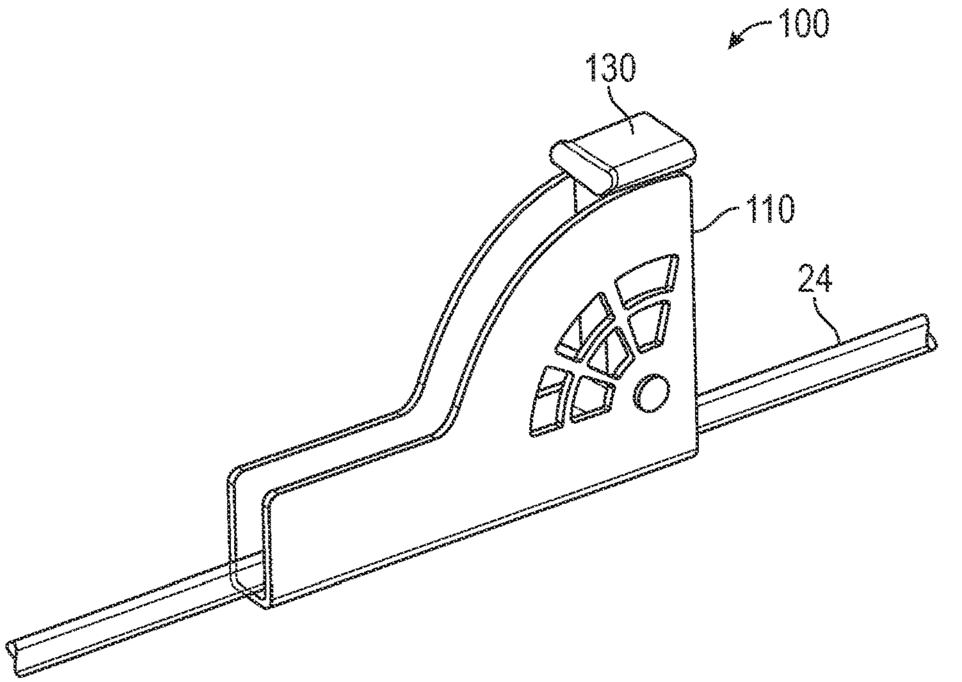
FIG. 3 depicts a perspective view of a levered flow regulation clamp assembly on an IV tube, according to aspects of the disclosure.
Figure 4:
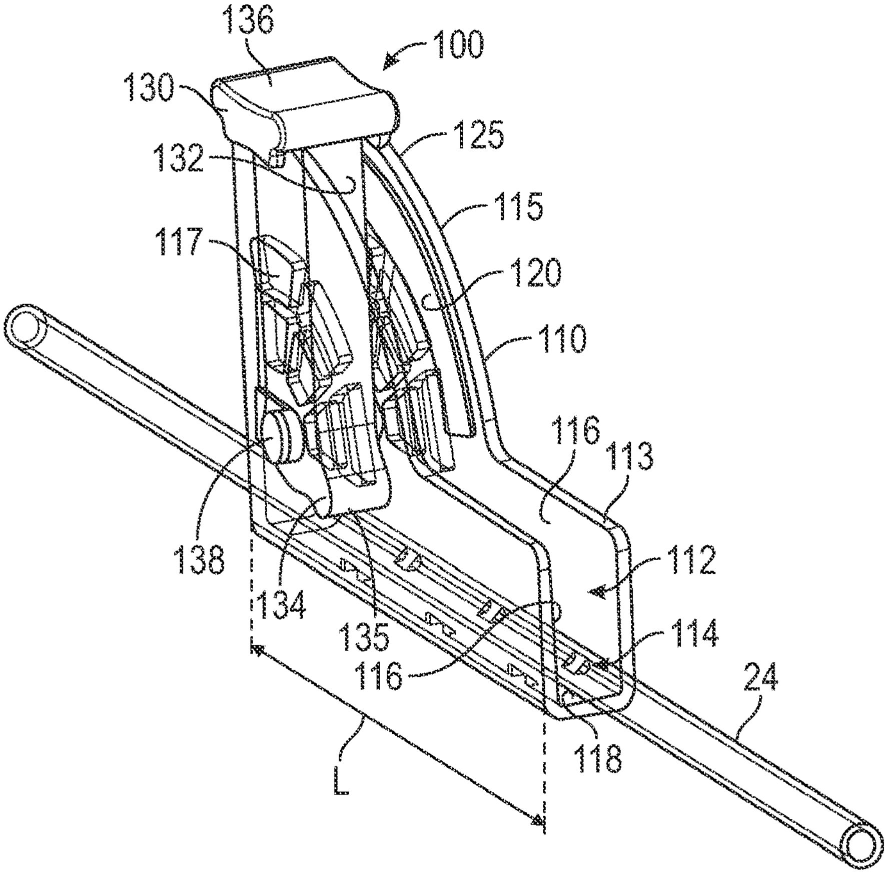
FIG. 4 depicts a perspective view of the levered flow regulation clamp assembly of FIG. 3, according to aspects of the disclosure.
Figure 5:
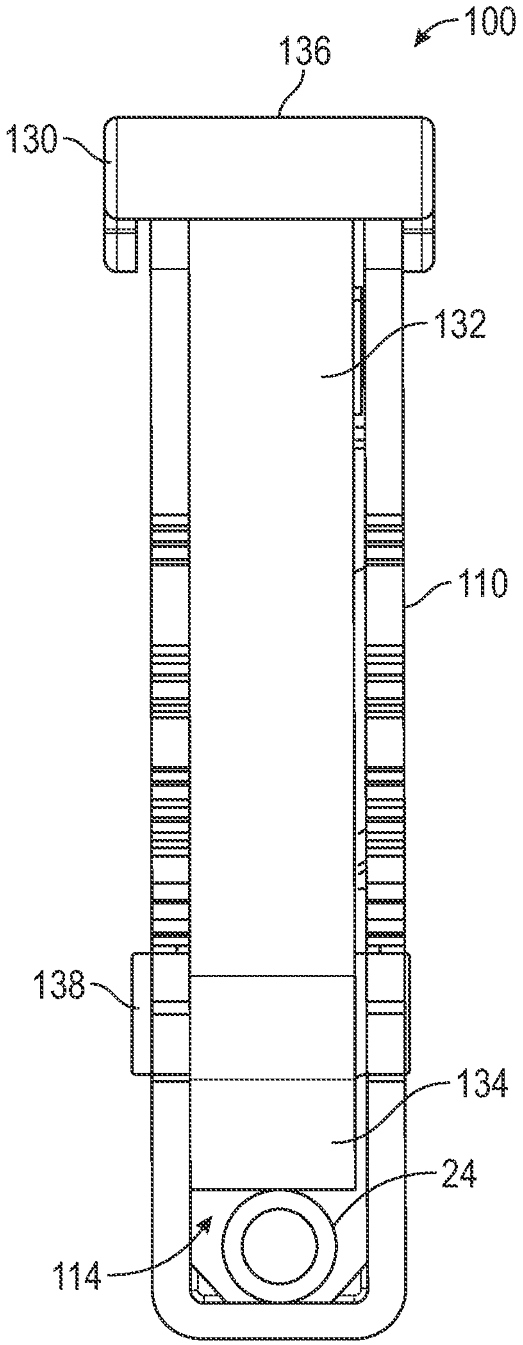
FIG. 5 depicts a front elevation view of the levered flow regulation clamp assembly of FIG. 3, according to aspects of the disclosure.
Figure 6:
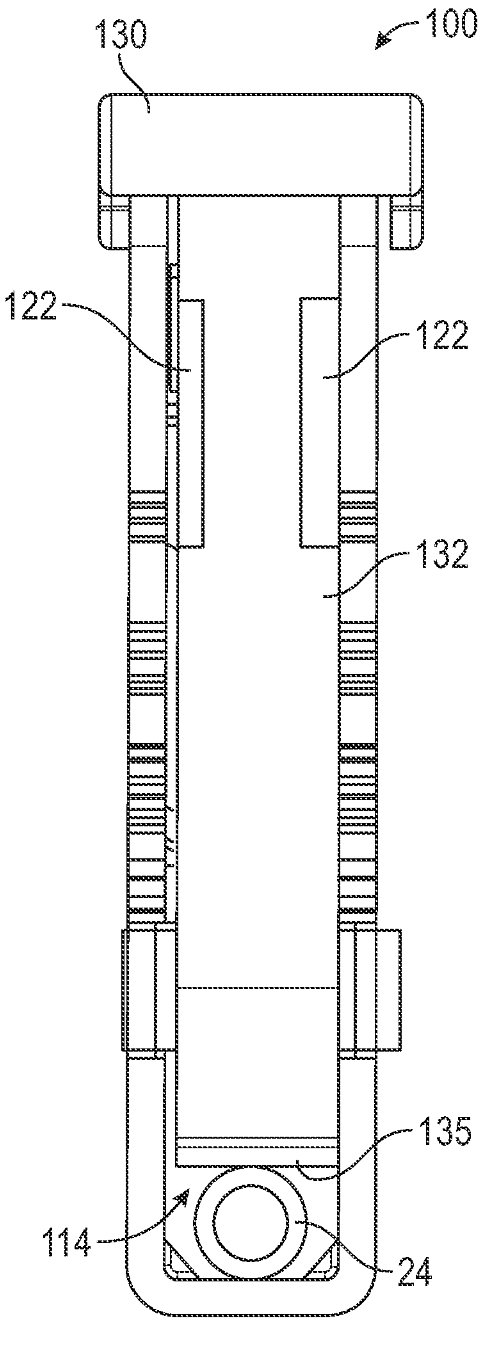
FIG. 6 depicts a rear view of the levered flow regulation clamp assembly of FIG. 3, according to aspects of the disclosure.
Figure 7:
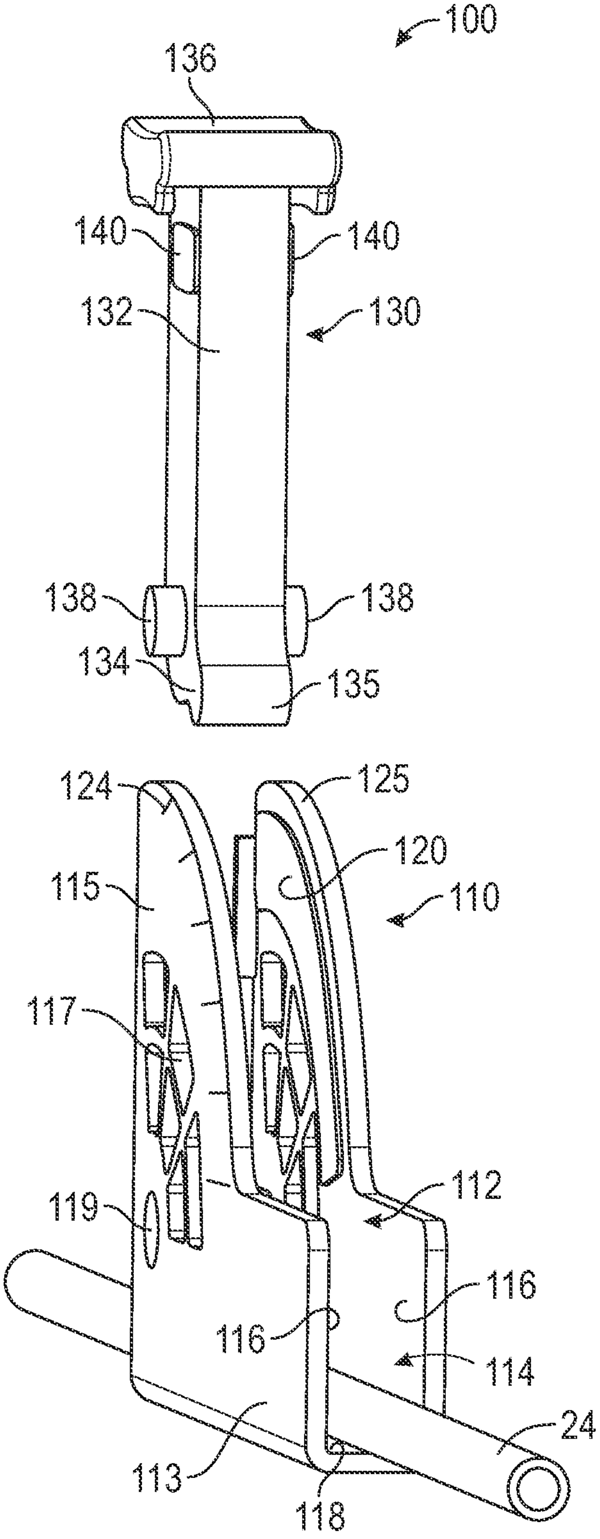
FIG. 7 depicts an exploded perspective view of the levered flow regulation clamp assembly of FIG. 3, according to aspects of the disclosure.

The roller clamp 26 illustrated in FIG. 2 has two opposing side walls 27 having a pair of guide grooves 30 that are aligned with each other and face each other. A flow-regulating roller 28 is provided having axially-projecting shafts 29 protruding from the centers of each side of the roller 28. The roller 28 is shown in outline for clarity. The shafts 29 of the roller 28 are captured by and seated in the guide grooves 30 so that the roller 28 can move up and down the guide grooves 30 as indicated by the arrows in FIG. 2.

The entire roller clamp 26 has four walls (see FIG. 1) in an open-ended boxlike construction and is dimensioned and configured to receive the connector tube 24. In use, the tube 24 passes through the roller clamp 26, between the two opposing side walls 27, the roller 28 and a guide wall 31 that is opposed to the roller 28.

In the roller clamp 26, the surface of the guide wall 31 converges along its length toward the position of the guide grooves 30 in the downward direction of the guide grooves 30 (e.g., in the direction of the arrows in FIG. 2). This tends to urge the connector tube 24 within the roller clamp 26 toward the guide grooves 30 and thus toward roller 28.

Thus, rolling the roller 28 downwardly along the guide grooves 30 in the direction of the gradually closer guide wall 31 in the direction of the arrows causes the roller 28 to impinge against the connector tube 24. As the roller 28 impinges on the tube 24, the tube 24 becomes squeezed, as it is a flexible material such as PVC, and the lumen of the infusion tube 24 therefore becomes smaller. In this way, by narrowing of the lumen, the flow rate of liquid passing through the connector tube 24 can be regulated.

Thus, the roller clamp 26 controls the flow rate through the infusion tube 24 by clamping the infusion tube 24 between the roller 28 and the guide wall 31. As discussed above, this provides for a course flow rate change because a small movement of the roller 28 causes a large change in the flow rate of the fluid through the tube 24. Also, the force of the fluid in the tube 24 exerts a biasing force against the roller 28, which often leads to slippage of the roller 28 (e.g., the roller 28 rolls back) from the adjusted position. Accordingly, it is desirable to have a flow regulation clamp design having structural stability with the ability to control the flow consistently without variation in adjusted flow rate.

With reference to FIGS. 3-10, a levered flow regulation clamp assembly 100 is shown. The levered flow regulation clamp assembly 100 includes a cam profile to pinch a tube 24 to provide improved control of flow regulation. A hinge and lever mechanism creates mechanical s for the levered flow regulation clamp assembly 100. The mechanical leverage reduces the need for sustaining frictional force to keep the lever in the desired position. The levered flow regulation clamp assembly 100 has a housing 110 and a slider 130.

The housing 110 has an open-ended construction and is dimensioned and configured to receive tubing, such as connector tube 24. A housing channel 112 may be configured as a U-shaped channel disposed through the entire length L of the housing 110. The housing channel 112 has two opposing side walls 116 and a bottom wall 118, where the bottom portion of the housing channel 112 defines a tube channel 114. The tube channel 114 is configured to receive an IV tube such as tube 24.

Each side wall 116 includes a substantially rectangular portion 113 and a curvilinear portion 115 (e.g., one quarter circle). One or more window openings 117 (e.g., viewing windows) and an axle opening 119 are disposed in each curvilinear portion 115. One or more friction pads 120 are disposed on the curvilinear portion 115 of each side wall 116. For example, the friction pad 120 shown in FIGS. 3-10 is a curved strip generally matching the shape of an outer perimeter 125 of the curvilinear portion 115. Each curvilinear portion 115 also includes a stop member 122 extending into the housing channel 112, the stop members 122 configured to prevent the slider 130 from moving outside of the housing channel 112 in the open position direction.

The slider 130 (e.g., lever) has a body 132 configured to rotate in the housing channel 112. The body 132 has a cam 134 that is sized and shaped to be disposed in the housing channel 112 and outside the tube channel 114 in an open position of the levered flow regulation clamp assembly 100, and to increasingly move into the tube channel 114 from an initial flow regulation position to a closed position of the levered flow regulation clamp assembly 100. A contact surface 135 of the cam 134 is configured to come into contact with the tube 24, where the cam 134 increasingly impinges on the tube 24 from the initial flow regulation position to the closed position.

The body 132 also has a gripping portion that extends out past the curvilinear portions 115 of the housing 110. The gripping portion 136 provides a gripping and/or engagement area for a user's thumb or finger to manipulate the slider 130. For example, the depicted gripping portion 136 has an indented/curved T-shape providing ergonomic surfaces for being pushed or pulled. The body 132 has opposing axles 138 that are received by the axle openings 119, where each axle 138 is configured to rotate within the associated axle opening 119. Friction pads 140 may be disposed on the body 132 of the slider 130 and positioned so that the friction pads 140 engage/interact with friction pads 120 of the housing 110. In aspects of the disclosure, the levered flow regulation assembly 100 may have only friction pads 120 on the housing 110, only friction pads 140 on the slider 130, or both. In aspects of the disclosure, the levered flow regulation assembly 100 may have a friction pad 120 on only one side wall 116 of the housing 110 and a friction pad 140 on only the corresponding side of the slider 130, or the friction pads 120, 140 may be on both side walls 116 and both sides of the slider 130, respectively.

In use, the tube 24 passes through the levered flow regulation assembly 100, between the two opposing side walls 116 and bottom wall 118 of the tube channel 114 and the bottom of the slider 130. Rotating the slider 130 in the appropriate direction (e.g., clockwise, counterclockwise) causes the cam 134 to move towards the tube 24, causing the contact surface 135 (e.g., the outer surface of the cam 134) to impinge against the tube 24. As the cam 134 impinges on the tube 24, the tube 24 becomes squeezed, as it is a flexible material such as PVC, and the lumen of the infusion tube 24 therefore becomes smaller. In this way, by narrowing of the lumen, the flow rate of liquid passing through the connector tube 24 can be regulated. The process may be reversed as well by rotating the slider 130 in the opposing direction, causing the cam 134 to move in a direction away from the tube 24 and decreasing the impingement of the tube 24.

Figure 8:
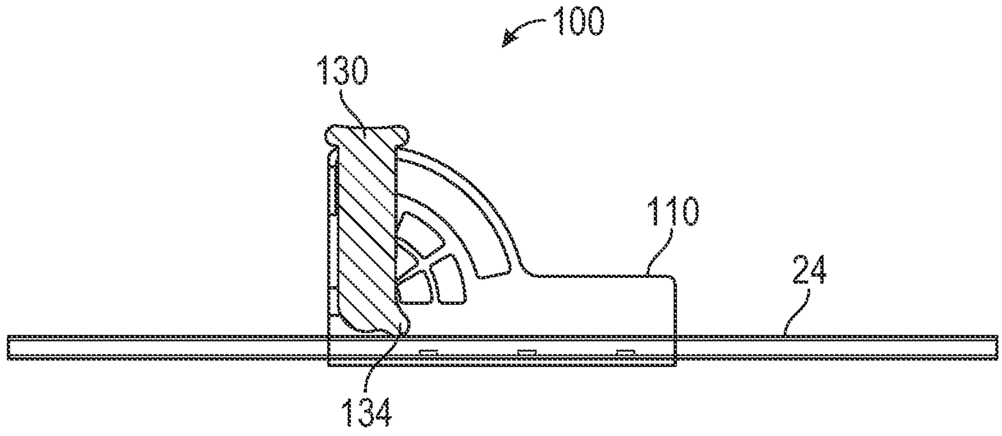
FIG. 8 depicts a cross-sectional side view of the levered flow regulation clamp assembly and tube of FIG. 3 in an open flow position, according to aspects of the disclosure.
Figure 9:
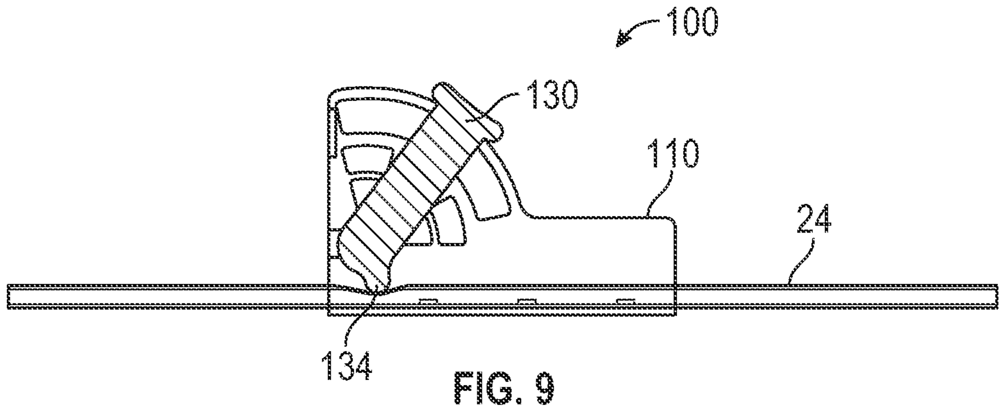
FIG. 9 depicts a cross-sectional side view of the levered flow regulation clamp assembly and tube of FIG. 3 in a regulated flow position, according to aspects of the disclosure.
Figure 10:
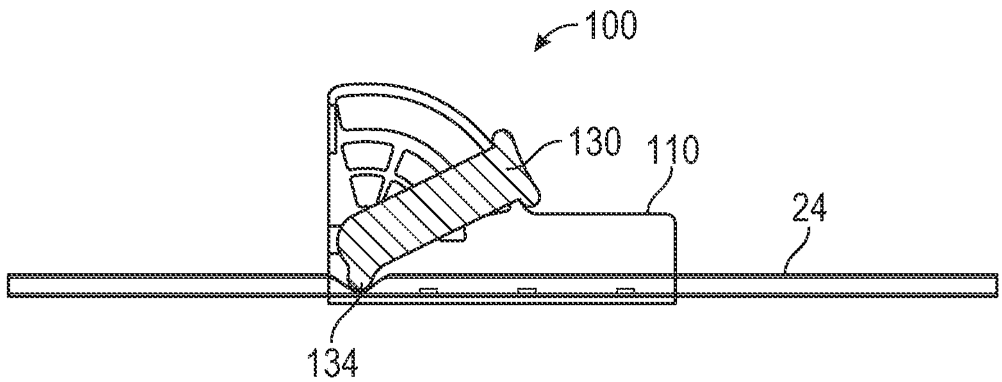
FIG. 10 depicts a cross-sectional side view of the levered flow regulation clamp assembly and tube of FIG. 3 in a closed flow position, according to aspects of the disclosure.

Also in use, the gripping portion 136 of the slider 130 may be aligned in a particular orientation according to scale markings 124 on the curvilinear portions 115 of the housing 110. Here, the scale markings 124 may indicate different levels of occlusion of the tube 24 associated with different fluid flow rates through the tube 24. For example, a $\frac{1}{8}^{th}$ rotation of the slider 130 may cause a specific linear length (e.g., X mm) of downward impingement of the cam 134. Also, the contact area with the tube 24 may be a portion of the contact surface 135 of the cam 134, where the cam 134 may be somewhat semicircular in shape as shown in FIGS. 8-10. According to aspects of the disclosure, the cam 134 may have any suitable shape, such as triangular, square or rectangular, for example.

In addition, by configuring the size and shape of the body 132 and the friction pads 120 to obtain a desired level of frictional engagement between the body 132 and the friction pads 120, the levered flow regulation assembly 100 may be self-locking. Thus, the slider 130 maintains its engagement position with the tube 24 during use (e.g., fluid flow in tube 24) because the frictional force between the body 132 and the friction pads 120 is greater than the rotational tendency of the cam 134 due to fluid forces pushing the tube 24 against the contact surface 135.

Further in use, the levered flow regulation assembly 100 may have different modes of operation. For example, an initial setting (e.g., factory setting) may have the slider 130 in a clearance position where there is clearance between the tube 24 and the contact surface 135 of the cam 134. Here, the levered flow regulation assembly 100 can slide freely on the tube 24, allowing the levered flow regulation assembly 100 to be positioned at a desired location on the tube 24 (e.g., a set distance from a drip chamber 22).

In a variety of intermediate use settings, the slider 130 is rotated about the axles 138 to adjust the fluid flow rate in the tube 24. As the slider 130 is rotated in a tightening direction (e.g., clockwise), the contact surface 135 of the cam 134 comes into contact with the tube 24 and proceeds to increasingly push into (e.g., occlude) the tube 24 as the slider 130 continues to rotate, thus further decreasing the fluid flow rate through the tube 24.

In a closed setting, the slider 130 is rotated as far as necessary (e.g., where the gripping portion 136 of the slider 130 contacts the rectangular portions 113 of the side walls 116) to cause the cam 134 to completely close (e.g., pinched closed) the tube 24 so that negligible or no fluid flows through the tube 24. Thus, the levered flow regulation assembly 100 is easy to operate, very stable while controlling the fluid flow rate in the tube 24 and provides for an accurate measurement of fluid flow compared to typical roller clamp designs.

The levered flow regulation assembly 100 may be easily assembled, according to aspects of the disclosure. For example, the housing 110 may be positioned in an assembly fixture (not shown) and the slider 130 inserted into the housing 110 so that the axles 138 are inserted into the axle openings 119. In aspects of the disclosure, the axles 138 may be swaged to maintain positive assembly of the levered flow regulation assembly 100. Next, the slider 130 may be positioned so that the body 132 contacts the stop members 122 and the levered flow regulation assembly 100 is in an open position. The levered flow regulation assembly 100 may then be slidingly mounted on a tube 24 as part of an IV set.

Each of the housing 110 and slider 130 may be integral one-piece components that are molded for efficient and low cost mass manufacturing, though any suitable manufacturing process may be used. The housing 110 and the slider 130 may be formed of any suitable material (PC, PP, and the like). These materials may be pliable after forming, which is useful for assembly, as well as durable, easily moldable and low cost. In aspects of the disclosure, the friction pads 120, 140 may be overmolded onto the housing 110 and the slider 130, respectively. In aspects of the disclosure, the friction pads 120, 140 may be adhesively coupled to the housing 110 and the slider 130, respectively.

In aspects of the disclosure, the size of the levered flow regulation assembly 100 may be generally the same as typical roller clamps used in the clinical community, the relative positions of fully open and fully closed positions of the levered flow regulation assembly 100 may be similar to typical roller clamps (e.g., up is open, down is closed), and the levered flow regulation assembly 100 has gravity direction independence (e.g., it can be positioned facing either direction on the tube 24). In aspects of the disclosure, the friction pads 120, 140 may be any suitable material (e.g., rubber, silicon) that provide resistance to movement of the slider 130 within the housing 110, which prevents deviation from a set fluid flow rate. In aspects of the disclosure, the cam 134 is actuated when the slider 130 is moved along the curvilinear portions 115 of the housing 110 (e.g., quarter circle movement).

Figure 11:
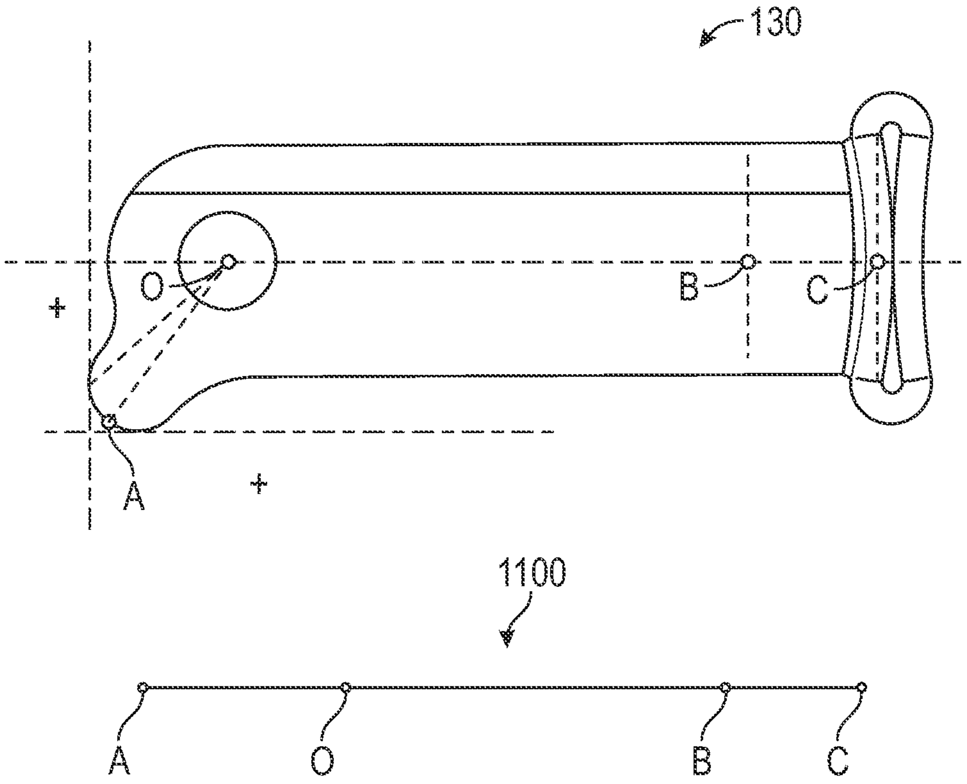
FIG. 11 depicts a schematic view of points where forces are applied on the lever of the levered flow regulation clamp assembly of FIG. 3, according to aspects of the disclosure.

As shown in the top portion of FIG. 11, the slider 130 may have multiple points A, O, B, C where forces are applied during use. These force points A, O, B, C are depicted linearly as shown on graph 1100 in the bottom portion of FIG. 11.

Figure 12:
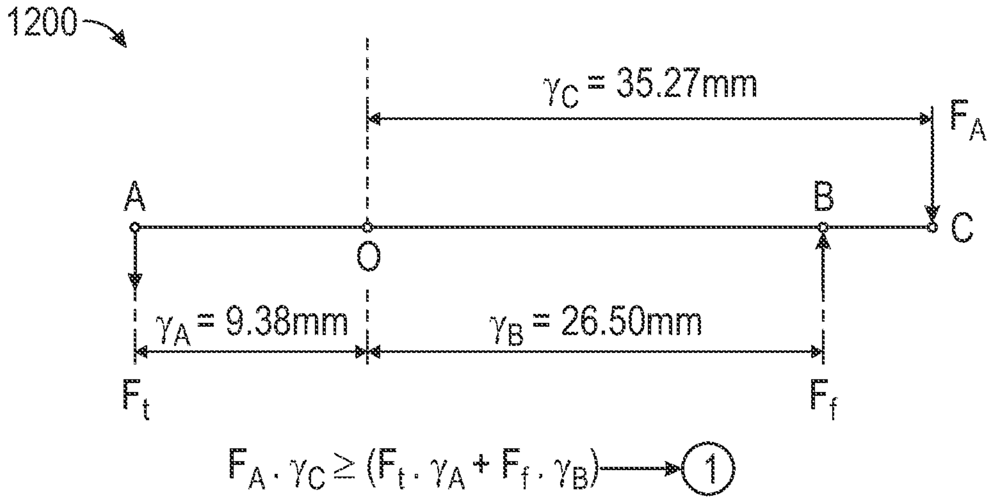
FIG. 12 depicts a table of calculations for locking the levered flow regulation clamp assembly of FIG. 3, according to aspects of the disclosure.
Figure 13:
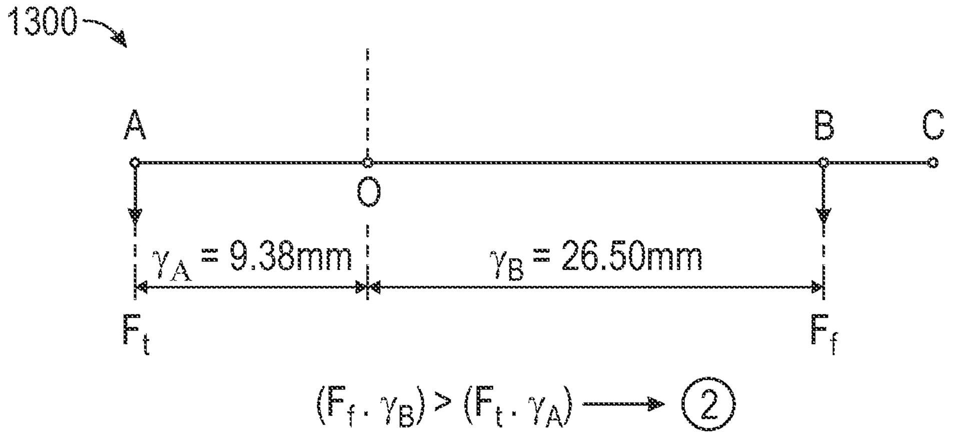
FIG. 13 depicts a table of calculations for the levered flow regulation clamp assembly of FIG. 3 in a locked position, according to aspects of the disclosure.
Figure 14:
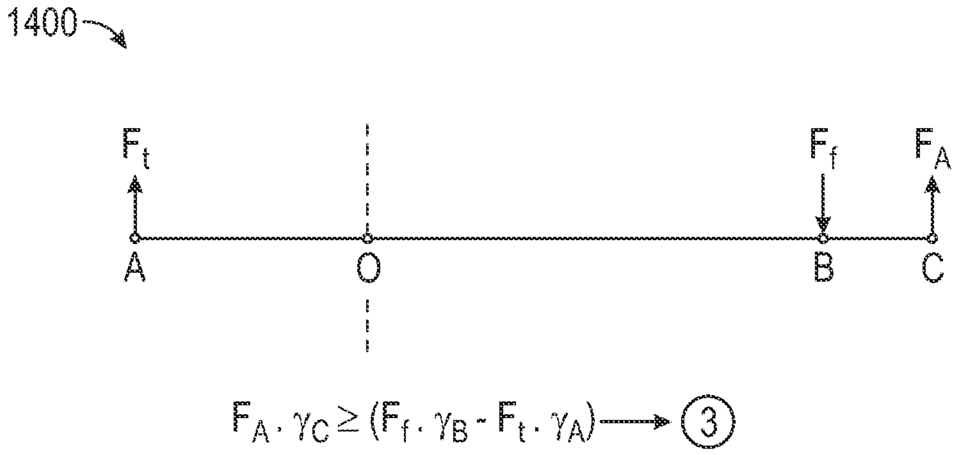
FIG. 14 depicts a table of calculations for unlocking the levered flow regulation clamp assembly of FIG. 3, according to aspects of the disclosure.

As shown in FIGS. 12-14, calculation charts 1200, 1300, 1400 show sample leverage calculations using the linearly depicted force points for operation of the levered flow regulation assembly 100 in a locking process, in a locked condition and in an unlocking process. Here, parametric analysis provides a minimized (e.g., optimal) size of the levered flow regulation assembly 100 based on constraint equations derived from the free body analysis shown in charts 1200, 1300, 1400.

In aspects of the disclosure, the levered flow regulation assembly 100 is configured to operate within clinical requirements of typical roller clamps. For example, the levered flow regulation assembly 100 is operable with one hand to provide a desired travel range for flow regulation (e.g., drip start to 246 drips/minute), where the travel may be minimally greater than 10 mm with a target travel greater than 12 mm and an optimal travel greater than 14 mm. As another example, a force required to close (e.g., stiffness) may be a minimum of less than 30 N with a target closing force of less than 20 N and an optimal closing force less than 20 N. Similarly, a force required to open (e.g., stiffness) may be a minimum of less than 40 N with a target opening force of less than 30 N and an optimal opening force less than 20 N. In yet another metric, a force required to operate (e.g., stiffness) may be a minimum of less than 30 N with a target operating force of less than 20 N and an optimal operating force less than 20 N.

In aspects of the disclosure, the levered flow regulation assembly 100 reduces clamp drift over time and provides a non-discrete flow setting, thus not limiting the flow rate to the design of the component. In aspects of the disclosure, the levered flow regulation assembly 100 has a slider 130 with a gripping portion 136 (e.g., top surface) where the operator's finger/thumb can rest while setting the flow rate. The slider 130 also has a friction pad 140 and behaves like a lever when force is applied on the tube 24 (e.g., IV line). Thus, when the flow rate has to be set, the operator places a finger or thumb on the gripping portion 136 of the slider 130 and rotate the slider 130 about its axis, resulting in the other end of the slider 130 (e.g., cam 134) applying a force on the tube 24, thus varying the flow rate.

Once the desired flow rate is set, the slider 130 is held in position by the friction pad 120, 140 interaction of the slider 130 and the housing 110. In this position, the torque exerted by the tube 24 on the slider 130 is counteracted by the torque applied by the friction pads 120, 140. Here, since the distance from the axis of rotation to the friction pad 140 on the slider 130 is significantly greater than that of the tube 24 to the axis, the frictional force required to balance the tube force is significantly lower. When the flow rate is to be increased, the operator places a finger/thumb on the gripping portion 136 of the slider 130 and rotates the slider 130 away from the tube 24, which reduces the force on the tube 24 and thus increases the flow rate.

Figure 15:
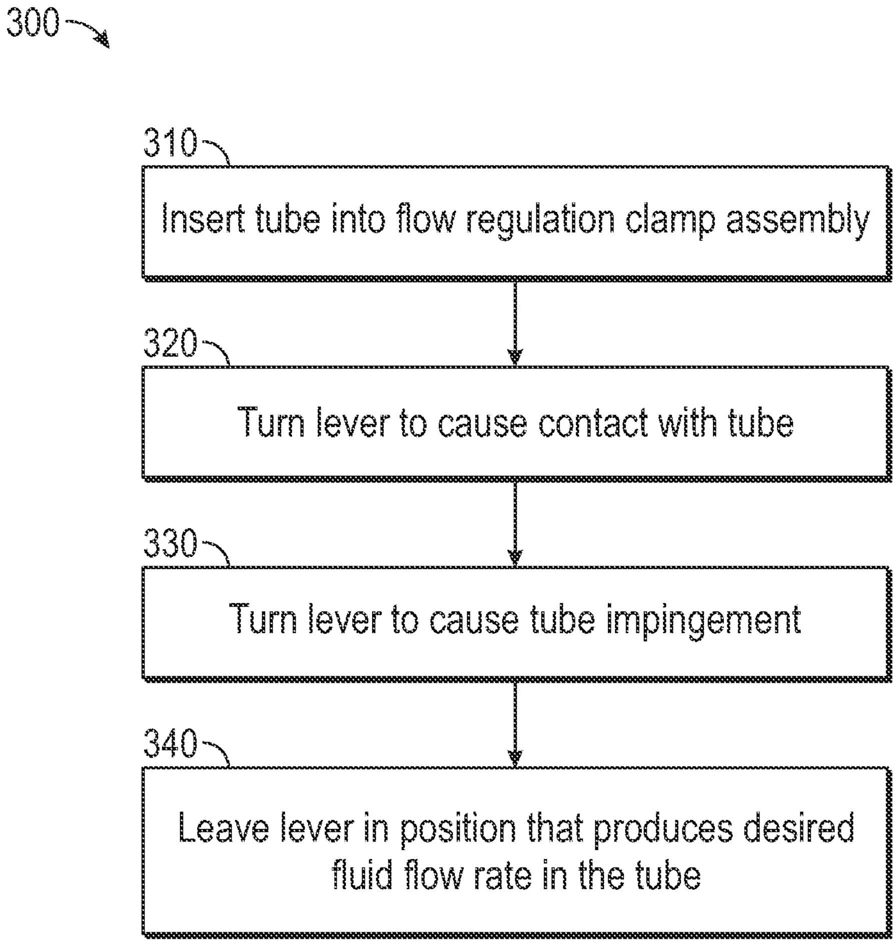
FIG. 15 depicts a schematic flow of a method of operating a levered flow regulation clamp assembly with an IV tube, according to aspects of the disclosure.

With reference to FIG. 15, a method 300 of operating a levered flow regulation clamp assembly is provided. In step 310, tubing (e.g., tube 24) is placed or disposed in a flow regulation clamp assembly (e.g., levered flow regulation clamp assembly 100) with the flow regulation clamp assembly in an open flow position (e.g., slider 130 contacting stop members 122 where the cam is not contacting the tube 24 or contacting but not impinging the tube 24). A lever (e.g., slider 130) is turned/rotated to cause the tube to be contacted by a portion of the levered flow regulation clamp assembly (e.g., contact surface 135 of cam 134 contacts tube 24), in step 320. In step 330, the lever is turned/rotated further to occlude the tube to cause tube impingement to reach a desired fluid flow rate (e.g., the cam 134 impinges tube 24 to restrict the interior volume of the tube 24). When the desired fluid flow rate is achieved, the lever is left in place without the need for locking or securing members (e.g., frictional force between friction pads 120, 140 keeps slider 130 in place), in step 340.

In one or more embodiments of the disclosure, a levered flow regulation clamp assembly comprises: a housing having an open-ended structure and comprising: two opposing side walls, each side wall comprising a rectangular bottom portion and a curvilinear top portion; and a bottom wall connecting the side walls, the side walls and the bottom wall defining a housing channel, and a bottom portion of the housing channel defining a tube channel configured to receive an intravenous tube; and a slider coupled to the housing, the slider comprising: a body; a cam disposed at a first end of the body; a gripping portion disposed at a second end of the body; and two opposing axles rotatably disposed within associated axle openings in the opposing side walls of the housing, wherein the body of the slider is configured to rotate about the opposing axles in the housing channel between an open position and a closed position.

In aspects of the disclosure, at least one curvilinear top portion comprises one or more window openings providing a view into the housing channel. In aspects of the disclosure, a friction pad is configured to provide a defined level of frictional engagement between the body of the slider and a curvilinear top portion. In aspects of the disclosure, the friction pad is disposed on a surface of the body of the slider facing an inside surface of the curvilinear top portion. In aspects of the disclosure, the friction pad is disposed on an inside surface of the curvilinear top portion. In aspects of the disclosure, the friction pad is a curvilinear strip matching a shape of a curved perimeter of the curvilinear top portion. In aspects of the disclosure, another friction pad is disposed on a surface of the body of the slider facing the friction pad disposed on the inside surface of the curvilinear top portion. In aspects of the disclosure, the friction pad is configured to maintain an engagement position of the slider relative to the intravenous tube during fluid flow through the intravenous tube. In aspects of the disclosure, the levered flow regulation clamp assembly is configured to be self-locking based on a frictional force from the friction pad being greater than a rotational tendency of the cam from fluid forces pushing the intravenous tube against the cam.

In aspects of the disclosure, the gripping portion of the slider extends out past the top curvilinear portions of the housing and is configured to provide a surface for being one of pushed and pulled by external force. In aspects of the disclosure, a plurality of scale markings are disposed on an outside surface of at least one of the curvilinear portions, the scale markings configured to indicate levels of occlusion of an intravenous tube disposed within the tube channel, each level of occlusion associated with a fluid flow rate through the intravenous tube. In aspects of the disclosure, when the slider is in the open position, the levered flow regulation assembly is configured to slide freely on the intravenous tube. In aspects of the disclosure, when the slider is in the open position, the cam is one of not touching the intravenous tube and lightly contacting the intravenous tube for full fluid flow through the intravenous tube. In aspects of the disclosure, when the slider is in the closed position, the cam is fully impinging the intravenous tube for no fluid flow through the intravenous tube. In aspects of the disclosure, at least one top curvilinear portion comprises a stop member extending into the housing channel, the stop member configured to prevent the slider from rotating outside of the housing channel past the open position. In aspects of the disclosure, a top surface of at least one bottom rectangular portion comprises a stop surface configured to prevent the second end of the body of the slider from rotating into the tube channel past the closed position.

In one or more embodiments of the disclosure, an infusion set comprises: a drip chamber; a connector tube; and a levered flow regulation clamp assembly, comprising: a housing having an open-ended structure and comprising: two opposing side walls, each side wall comprising a rectangular bottom portion and a curvilinear top portion; and a bottom wall connecting the side walls, the side walls and the bottom wall defining a housing channel, and a bottom portion of the housing channel defining a tube channel configured to receive an intravenous tube; and a slider coupled to the housing, the slider comprising: a body; a cam disposed at a first end of the body; a gripping portion disposed at a second end of the body; and two opposing axles rotatably disposed within associated axle openings in the opposing side walls of the housing, wherein the body of the slider is configured to rotate about the opposing axles in the housing channel between an open position and a closed position.

In aspects of the disclosure, a friction pad is configured to provide a defined level of frictional engagement between the body of the slider and a curvilinear top portion, wherein the levered flow regulation clamp assembly is configured to be self-locking based on a frictional force from the friction pad being greater than a rotational tendency of the cam from fluid forces pushing the intravenous tube against the cam. In aspects of the disclosure, at least one top curvilinear portion comprises a stop member extending into the housing channel, the stop member configured to prevent the slider from rotating outside of the housing channel past the open position, and wherein a top surface of at least one bottom rectangular portion comprises a stop surface configured to prevent the second end of the body of the slider from rotating into the tube channel past the closed position.

In one or more embodiments of the disclosure, a method of operating a levered flow regulation clamp assembly comprises: disposing an intravenous tube within the levered flow regulation clamp assembly by extending the intravenous tube through a length of a bottom portion of a housing channel defining a tube channel; engaging a gripping portion of a slider coupled to the housing, the slider being in an open flow position in which the slider is one of not contacting the intravenous tube and contacting but not impinging the intravenous tube to provide full fluid flow through the intravenous tube; rotating the slider in a first rotational direction along a top curvilinear portion of the housing channel to a desired flow position, thus rotating a cam disposed on an end of the slider downward into the tube channel a defined distance of travel associated with a degree of rotation of the slider; pushing a contact surface of the cam into the intravenous tube the defined distance of travel, thus occluding the intravenous tube a defined amount associated with a defined reduced fluid flow rate through the intravenous tube; and leaving the slider in the desired flow position, wherein the slider is self-locking based on a frictional force from a friction pad disposed on at least one of the slider and the top curvilinear portion of the housing channel, the frictional force being greater than a rotational tendency of the cam from fluid forces pushing the intravenous tube against the cam.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A levered flow regulation clamp assembly comprising:

a housing having an open-ended structure and comprising:

two opposing side walls, each side wall comprising a rectangular bottom portion and a curvilinear top portion extending upward from an uppermost surface of the rectangular bottom portion; and a bottom wall connecting the side walls, the side walls and the bottom wall defining a housing channel, and a bottom portion of the housing channel defining a tube channel configured to receive an intravenous tube; and a slider coupled to the housing, the slider comprising:

a body;

a cam disposed at a first end of the body;

a gripping portion disposed at a second end of the body; and two opposing axles rotatably disposed within associated axle openings in the opposing side walls of the housing, wherein the body of the slider is configured to rotate about the opposing axles in the housing channel between an open position and a closed position, wherein the uppermost surface of at least one rectangular bottom portion comprises a stop surface configured to prevent the second end of the body of the slider from moving past a bottommost portion of the curvilinear top portion into the tube channel within the rectangular bottom portion and past the closed position.

2. The levered flow regulation clamp assembly of claim 1, wherein at least one curvilinear top portion comprises one or more window openings providing a view into the housing channel.

3. The levered flow regulation clamp assembly of claim 1, further comprising a friction pad configured to provide a defined level of frictional engagement between the body of the slider and a curvilinear top portion.

4. The levered flow regulation clamp assembly of claim 3, wherein the friction pad is disposed on a surface of the body of the slider facing an inside surface of the curvilinear top portion.

5. The levered flow regulation clamp assembly of claim 3, wherein the friction pad is disposed on an inside surface of the curvilinear top portion.

6. The levered flow regulation clamp assembly of claim 5, wherein the friction pad is a curvilinear strip matching a shape of a curved perimeter of the curvilinear top portion.

7. The levered flow regulation clamp assembly of claim 5, wherein another friction pad is disposed on a surface of the body of the slider facing the friction pad disposed on the inside surface of the curvilinear top portion.

8. The levered flow regulation clamp assembly of claim 3, wherein the friction pad is configured to maintain an engagement position of the slider relative to the intravenous tube during fluid flow through the intravenous tube.

9. The levered flow regulation clamp assembly of claim 8, wherein the levered flow regulation clamp assembly is configured to be self-locking based on a frictional force from the friction pad being greater than a rotational tendency of the cam from fluid forces pushing the intravenous tube against the cam.

10. The levered flow regulation clamp assembly of claim 1, wherein the gripping portion of the slider extends out past the top curvilinear portions of the housing and is configured to provide a surface for being one of pushed and pulled by external force.

11. The levered flow regulation clamp assembly of claim 1, wherein a plurality of scale markings are disposed on an outside surface of at least one of the curvilinear portions, the scale markings configured to indicate levels of occlusion of an intravenous tube disposed within the tube channel, each level of occlusion associated with a fluid flow rate through the intravenous tube.

12. The levered flow regulation clamp assembly of claim 1, wherein when the slider is in the open position, the levered flow regulation assembly is configured to slide freely on the intravenous tube.

13. The levered flow regulation clamp assembly of claim 1, wherein when the slider is in the open position, the cam is one of not touching the intravenous tube and lightly contacting the intravenous tube for full fluid flow through the intravenous tube.

14. The levered flow regulation clamp assembly of claim 1, wherein when the slider is in the closed position, the cam is fully impinging the intravenous tube for no fluid flow through the intravenous tube.

15. The levered flow regulation clamp assembly of claim 1, wherein at least one top curvilinear portion comprises a stop member extending into the housing channel, the stop member configured to prevent the slider from rotating outside of the housing channel past the open position.

16. An infusion set comprising:

a drip chamber;

a connector tube coupled to the drip chamber; and the levered flow regulation clamp assembly of claim 1 coupled to the connector tube.

17. The infusion set of claim 16, wherein the levered flow regulation clamp assembly further comprises a friction pad configured to provide a defined level of frictional engagement between the body of the slider and the curvilinear top portion, wherein the levered flow regulation clamp assembly is configured to be self-locking based on a frictional force from the friction pad being greater than a rotational tendency of the cam from fluid forces pushing the connector tube against the cam.

18. A method of operating the levered flow regulation clamp assembly of claim 1, the method comprising:

disposing the intravenous tube within the levered flow regulation clamp assembly by extending the intravenous tube through a length of the bottom portion of the housing channel defining the tube channel;

engaging the gripping portion of the slider coupled to the housing, the slider being in an open flow position in which the slider is one of not contacting the intravenous tube and contacting but not impinging the intravenous tube to provide full fluid flow through the intravenous tube;

rotating the slider in a first rotational direction along the top curvilinear portion of the housing channel to a desired flow position, thus rotating the cam disposed on the first end of the body of the slider downward into the tube channel a defined distance of travel associated with a degree of rotation of the slider;

pushing a contact surface of the cam into the intravenous tube the defined distance of travel, thus occluding the intravenous tube a defined amount associated with a defined reduced fluid flow rate through the intravenous tube; and leaving the slider in the desired flow position, wherein the slider is self-locking based on a frictional force from a friction pad disposed on at least one of the slider and the top curvilinear portion of the housing channel, the frictional force being greater than a rotational tendency of the cam from fluid forces pushing the intravenous tube against the cam.

19. The levered flow regulation clamp assembly of claim 1, wherein the curvilinear top portion is a quarter circle shape.

* * * * *